(12) United States Patent
Vissiere et al.

(10) Patent No.: US 11,280,928 B2
(45) Date of Patent: Mar. 22, 2022

(54) METHOD FOR LOCATING AN OBJECT MOVING IN A MAGNETIC FIELD GENERATED BY A SET OF AT LEAST THREE MAGNETIC GENERATORS

(71) Applicant: SYSNAV, Vernon (FR)

(72) Inventors: David Vissiere, Paris (FR); Mathieu Hillion, Vernon (FR); Hendrik Meier, Vernon (FR)

(73) Assignee: SYSNAV, Vernon (FR)

( * ) Notice: Subject to any disclaimer, the term of this patent is extended or adjusted under 35 U.S.C. 154(b) by 20 days.

(21) Appl. No.: 16/631,149

(22) PCT Filed: Jul. 17, 2018

(86) PCT No.: PCT/FR2018/051815
§ 371 (c)(1),
(2) Date: Jan. 14, 2020

(87) PCT Pub. No.: WO2019/016465
PCT Pub. Date: Jan. 24, 2019

(65) Prior Publication Data
US 2020/0225379 A1   Jul. 16, 2020

(30) Foreign Application Priority Data
Jul. 17, 2017   (FR) ..................................... 1756755

(51) Int. Cl.
*G01B 7/14*   (2006.01)
*G01B 7/30*   (2006.01)
(Continued)

(52) U.S. Cl.
CPC ............. *G01V 3/165* (2013.01); *G01B 7/004* (2013.01); *G01D 5/14* (2013.01); *G01D 5/145* (2013.01);
(Continued)

(58) Field of Classification Search
CPC ...... G01D 5/147; G01D 5/2451; G01D 5/145; G01D 5/14; G01B 7/003; G01B 7/30;
(Continued)

(56) References Cited

U.S. PATENT DOCUMENTS 3,868,565 A   2/1975 Kuipers
4,737,794 A   4/1988 Jones
(Continued)

FOREIGN PATENT DOCUMENTS

CN   104776865 A   7/2015

OTHER PUBLICATIONS

International Preliminary Report on Patentability received for PCT Patent Application No. PCT/FR2018/051815, dated Jan. 30, 2020, 16 pages (8 pages of English Translation and 8 pages of Original Document).
(Continued)

*Primary Examiner* — Raul J Rios Russo
(74) *Attorney, Agent, or Firm* — Womble Bond Dickinson (US) LLP

(57) ABSTRACT

The present invention relates to a method for locating an object (1) integral with a triaxial magnetic sensor (2) moving in a magnetic field generated by a set of at least three triaxial magnetic generators (3) static in a common reference frame, the method being characterised in that it includes the steps of:
(a) For each generator (3) determining as a function of magnetic field measurements acquired by the sensor (2) and associated with said generator (3) a position of said sensor (2) in said common reference frame;
(b) Calculating for each generator (3) a parameter representative of an error on said determined position of the sensor (2) for the generator (3);
(c) Selecting a sub-set of the set of generators (3) as a function of said parameters estimated for each of the
(Continued)

generators (3) said selected sub-set of the set of generators (3) including each generator (3) for which said estimated parameter is less than at least one reference threshold;

(d) Estimating the position of the object (1) by merging the determined positions of the sensor (2) for each generator (3) selected in said sub-set.

11 Claims, 2 Drawing Sheets

(51) Int. Cl.

| | |
|---|---|
| *G01V 3/165* | (2006.01) |
| *G01B 7/004* | (2006.01) |
| *G01R 33/02* | (2006.01) |
| *G01V 3/10* | (2006.01) |
| *G01V 3/38* | (2006.01) |
| *G01D 5/14* | (2006.01) |
| *G01D 5/245* | (2006.01) |
| *G01B 7/00* | (2006.01) |

(52) U.S. Cl.
CPC ........... *G01D 5/147* (2013.01); *G01D 5/2451* (2013.01); *G01R 33/0206* (2013.01); *G01V 3/104* (2013.01); *G01V 3/38* (2013.01); *G01B 7/003* (2013.01); *G01B 7/30* (2013.01)

(58) Field of Classification Search
CPC ........ G01B 7/004; G01V 3/165; G01V 3/104; G01V 3/38; G01R 33/0206; A61B 5/062
USPC ................... 324/51, 55, 200, 207.11, 207.22
See application file for complete search history.

(56) References Cited

U.S. PATENT DOCUMENTS

| | | |
|---|---|---|
| 4,945,305 A | 7/1990 | Blood |
| 5,307,072 A | 4/1994 | Jones, Jr. |
| 6,400,139 B1 | 6/2002 | Khalfin et al. |
| 6,636,757 B1 | 10/2003 | Jascob et al. |
| 8,311,767 B1 | 11/2012 | Stetson |
| 2002/0062203 A1* | 5/2002 | Gilboa ................ G01D 5/2086 |
| | | 702/150 |
| 2011/0004430 A1 | 1/2011 | Nieminen et al. |
| 2011/0153233 A1* | 6/2011 | Grenet ................ G01R 33/025 |
| | | 702/57 |
| 2011/0224537 A1 | 9/2011 | Brunner |
| 2015/0057969 A1 | 2/2015 | Hautson et al. |
| 2015/0226559 A1* | 8/2015 | Waite ....................... G05D 1/10 |
| | | 701/23 |
| 2016/0356601 A1* | 12/2016 | Lescourret .............. F41G 3/225 |
| 2017/0248423 A1* | 8/2017 | Youssef ................ G01C 21/08 |

OTHER PUBLICATIONS

International Search Report and Written Opinion received for PCT Patent Application No. PCT/FR2018/051815, dated Nov. 7, 2018, 18 pages (8 pages of English Translation and 10 pages of Original Document).

Preliminary Research Report received for French Application No. 1756755, dated Apr. 4, 2018, 3 pages (1 page of French Translation Cover Sheet and 2 pages of original document).

\* cited by examiner

METHOD FOR LOCATING AN OBJECT MOVING IN A MAGNETIC FIELD GENERATED BY A SET OF AT LEAST THREE MAGNETIC GENERATORS

GENERAL TECHNICAL FIELD

The present invention relates to the field of navigation without GPS.

More specifically, it relates to a method for locating an object moving in an artificial magnetic field.

PRIOR ART

Magnetic location designates a technique in which an object equipped with at least one magnetic field sensor is located in an artificial magnetic field, generated by at least one source. Magnetic location enables high precision (with an error that is sub-millimetric and below one degree). Applications are mainly found in the medical field, for example for surgical navigation.

The source, i.e. a magnetic field generator, typically contains three perpendicular coils which emit distinguishable magnetic fields, for example AC fields with different frequencies. The sensor also measures the magnetic fields along three axes. The signals of the sensor along its axes are thereafter demodulated with respect to the frequencies of the emitting coils. The data set resulting from this process and the control (modelling and calibration) of the magnetic field make it possible to calculate the position and the orientation of the sensor (or of a tool on which the sensor is fixed) in real time.

The technique for estimating the position and the orientation of an object by measuring the magnetic field emitted by a source with a magnetic sensor is well known since the 1970s, see for example the U.S. Pat. Nos. 3,868,565, 4,737,794, or 4,945,305.

The processing of the signal received by the sensor involves its breakdown into components derived from each of the coils of the source. This breakdown may be carried out using: (1) DC magnetic fields pulsed in such a way that the three coils of the source transmit a signal in turn (see for example the U.S. Pat. No. 4,945,305); (2) AC magnetic fields with different frequencies for the three coils of the source, making it possible to distinguish them by demodulation (see for example the U.S. Pat. No. 3,868,565). The breakdown of the signals received by the triaxial coils from the sensor with respect to the transmitting triaxial coils provides a matrix of 3×3=9 coefficients on the basis of which the position and the attitude (i.e. six degrees of freedom in total) of the sensor relative to the source may be calculated (see U.S. Pat. No. 4,737,794).

There are mainly two difficulties encountered in such source—sensor systems.

Firstly, since the magnetic field decreases with the cube of the source—sensor distance, the signal rapidly becomes weak and typically reaches noise level at a distance of around one metre for commercially available systems. There is thus a degradation in performance as a function of distance. Good precision can only be attained in a limited region around the source. One solution is to increase the size of the coils or to increase the current, which is in practice quickly limited.

Next, a magnetic field emitted by the source, whether it is pulsed DC or AC, is disturbed by (1) conductive materials (by the induction of Foucault currents) and (2) permeable materials, the two materials being able to be encountered in applications. Such disturbances falsify the measurements and degrade the performance.

For immobile disturbances, one possible solution is to draw up a map of the magnetic field according to a 3D network in space. This solution requires carrying out a calibration by an expert and is not practical at all in all situations where the disturbing objects such as tools are regularly displaced, which would require permanent recalibration.

Alternatively, it is proposed in the U.S. Pat. No. 6,636,757 to mount up to three triaxial sources on a "shield" which acts as an isolating element limiting the distortion of the magnetic field due to a disturbing metal object. An associated calibration method is provided. It is understood that such a solution is probably efficient but very cumbersome in practice.

In the U.S. Pat. No. 6,400,139, the use is proposed of a single source and two sensors: a "control" sensor and that of which the position is sought ("probe"), considered as a secondary AC field source. In other words, the proposed architecture is equivalent to an architecture with two sources and one sensor but in which the position of a source is sought, that of the sensor being known. An examination of the phase of the signal sensor makes it possible to separate the disturbances due to conductive materials, but not those of permeable materials.

In other documents, it is not attempted to correct the effect of a disturbance, but simply to detect it, see the applications US2011224537 or US2011004430.

It may be noted that the search for a solution that is at one and the same time applicable and without loss of performance or temporal resolution in a generic situation remains an open problem.

It would thus be desirable to have available a magnetic location method which is still as efficient, but furthermore completely robust against disturbances of any nature whatsoever.

DESCRIPTION OF THE INVENTION

The present invention thereby relates, according to a first aspect, to a method for locating an object integral with a triaxial magnetic sensor moving in a magnetic field generated by a set of at least three triaxial magnetic generators static in a common reference frame, the method being characterised in that it includes the steps of:
   (a) For each generator determining as a function of magnetic field measurements acquired by the sensor and associated with said generator a position of said sensor in said common reference frame;
   (b) Calculating for each generator a parameter representative of an error on said determined position of the sensor for the generator;
   (c) Selecting a sub-set of the set of generators as a function of said parameters estimated for each of the generators;
   (d) Estimating the position of the object by merging the determined positions of the sensor for each generator selected in said sub-set.

According to other advantageous and non-limiting characteristics:
the sensor and the generators are each constituted of three coils organised into triaxes;
step (b) includes for each generator the estimation of the values of two mathematical invariants as a function of the magnetic field measurements acquired by the sensor and associated with said generator;

said parameter representative of an error on said determined position of the sensor is calculated for each generator at step (b) as a function of the estimated values of said two mathematical invariants for said generator and theoretical values of said two mathematical invariants;

said parameter representative of an error on said determined position of the sensor is an estimation of said error on said determined position of the sensor;

said sub-set of the set of generators selected at step (c) includes each generator for which said estimated parameter is less than at least one reference threshold;

if said sub-set includes fewer than a predetermined minimum number of generators, said sub-set of the set of generators selected at step (c) further includes each generator for which said estimated parameter is less than at least one degraded threshold greater than the reference threshold;

the position obtained by merging is the average position of the determined positions of the sensor for each generator selected in said sub-set;

if said sub-set of the set of generators selected at step (c) includes at least one generator for which said estimated parameter is greater than said reference threshold, the position obtained by merging is the average position of the determined positions of the sensor for each generator of the largest sub-set of said sub-set of generators for which said estimated parameter remains less than said reference threshold;

the attitude is taken into account in addition to the position in steps (a) to (d).

According to a second aspect, the invention relates to a system including a triaxial magnetic sensor, a set of at least three triaxial magnetic generators static in a common reference frame, for locating an object integral with the sensor and moving in the magnetic field generated by said generators, characterised in that it includes data processing means configured to implement:

A module for determining, for each generator, as a function of magnetic field measurements acquired by the sensor and associated with said generator a position of said sensor in said common reference frame;

A module for calculating for each generator a parameter representative of an error on said determined position of the sensor for the generator;

A module for selecting a sub-set of the set of generators as a function of said parameters estimated for each of the generators;

A module for estimating the position of the object by merging the determined positions of the sensor for each generator selected in said sub-set.

According to a third and a fourth aspect, the invention relates to a computer programme product including code instructions for the execution of a method for locating an object integral with a triaxial magnetic sensor moving in a magnetic field generated by a set of at least three triaxial magnetic generators static in a common reference frame, according to the first aspect of the invention; and a storage means readable by a computer equipment on which a computer programme product includes code instructions for the execution of a method for locating an object integral with a triaxial magnetic sensor moving in a magnetic field generated by a set of at least three triaxial magnetic generators static in a common reference frame, according to the first aspect of the invention.

DESCRIPTION OF THE FIGURES

Other characteristics and advantages of the present invention will become clear from reading the description that follows of a preferential embodiment. This description will be given with reference to the appended drawings in which.

DETAILED DESCRIPTION

Architecture

Figure 1:
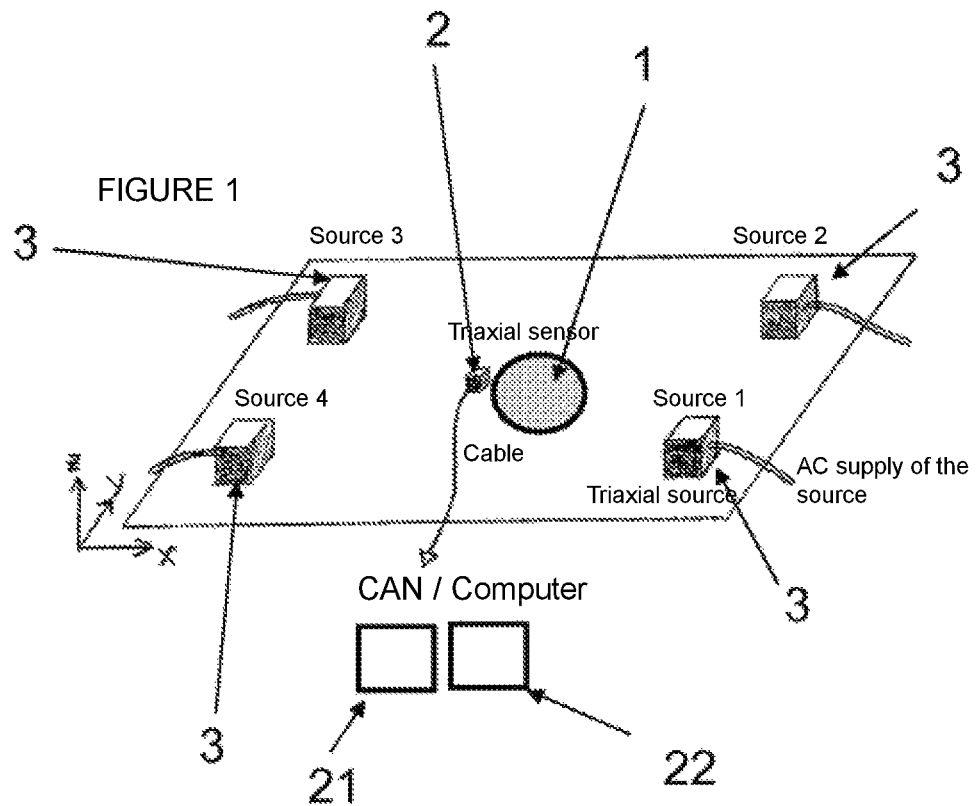
FIG. 1 is a diagram of a system for the implementation of the method according to the invention.

With reference to FIG. 1, the present method enables the location of an object 1 integral with a triaxial magnetic sensor 2 moving in a magnetic field (noted $\vec{B}$) generated by a set of at least three triaxial magnetic generators 3 (in the remainder of the present description, n will designate the number of generators 3, with n≤3, in the example of FIG. 1 n=4. One could go up to eight or ten generators 3 for results of very good quality without it being too difficult to distinguish the contributions of the different generators, see below).

Said triaxial magnetic generators 3 are static in a common reference frame, preferentially orthonormal, typically the terrestrial reference frame. This signifies that they are fixed and thus have predetermined positions with respect to each other. The triaxes are advantageously all oriented in accordance with said common orthonormal point of reference, i.e. that the three axes of each generator 3 correspond to the three axes of said common point of reference, so as to facilitate the calculations.

They are typically constituted of three axial coils organised into triaxes (i.e. each extending along one of the three axes). In a preferred manner, the generators (and even each of their coils) are associated with different and distinguishable frequencies (frequency of the alternating current supplying them), but it will be understood as explained in the introduction that the fields in the different generators can also for example be pulsed in turn.

It will be understood that this "artificial" magnetic field generated by the generators 3 generally falls within an ambient magnetic field (of natural origin), substantially static in said common reference frame, which is not generated by the generators 3 (typically the Earth's magnetic field), but it will be understood that this ambient field is negligible compared to the field generated by the generators, such that the latter could be considered alone.

As already explained, the magnetic field is a vector field in three dimensional space, that is to say associating a vector of three dimensions with each three-dimensional point in which the object is moveable.

This object 1 may be any moveable object of which knowledge of the position is desired, for example a wheeled vehicle, a drone, a tool, an instrument, etc., but also a person or a part of his body (his hands, etc.).

The object 1 is equipped with a triaxial magnetic sensor 2, i.e. magnetic measurement means, generally constituted of three axial coils (and generally speaking magnetometers) arranged in triaxes. More precisely, the sensor 2 is integral with the object 1, i.e. it has a movement substantially identical in the terrestrial reference frame. In a preferred manner, the reference frame of the object 1 is provided with an orthonormal cartesian point of reference in which the coordinates are noted $(x_1, x_2, x_3)$, the sensor 20 thus has a predetermined and fixed position in this point of reference.

In a preferred manner, the orthonormal point of reference associated with the object 1 is chosen by convention (and by facility for the remainder of the present description) such that the triaxis of the sensor 2 is advantageously oriented in accordance with said orthonormal point of reference associated with the object 1, i.e. that the three axes of the sensor 2 correspond to the three axes of said point of reference of the object 1, so as to facilitate the calculations.

But those skilled in the art will know in all cases how to transpose it to any spatial arrangement of the generators 3 and sensors 2.

The system may include processing means 21 (typically a processor) for the implementation directly in real time of the processing operations of the present method, or instead the measurements may be transmitted via communication means to an external device such as a remote server, or instead the measurements may be recorded in local data storage means 22 (a flash type memory for example) for potential a posteriori processing.

In the example of FIG. 1, the sensor 2 and the generators 3 are arranged on a table, which is equipped with processing means 21, with which they are connected via a wired connection.

If it is a remote equipment (such as a server) that hosts the "intelligence", it includes dedicated processing means such as a processor for implementing the processing operations of the present method that are going to be described.

In the remainder of the present description, it will be seen that the local data processing means or a remote equipment may indifferently and according to the applications carry out all or part of the steps of the method.

Mono-Source Position Determination

In a first step (a), the method includes the determination, for each generator 3, of a position of said sensor 2 in said common reference frame as a function of magnetic field measurements acquired by the sensor 2 and associated with said generator 3. Step (a) also advantageously includes the determination, for each generator 3, of an attitude (i.e. an orientation) of said sensor 2 in said common reference frame.

In other words, n positions/attitudes are independently determined. Each of these determinations of position/attitude is advantageously compliant with the "mono-source" prior art, which comprises a generator consisting of three orthogonal coils and a sensor also of three triaxial coils. In other words, each position/attitude is calculated as if the associated generator 3 was alone.

Each "sub-system" generator—sensor of the present multi-source system—is thus typically equivalent to a mono-source system such as described in the U.S. Pat. No. 4,737,794. It enables location in a limited region around the source, for example with the methods disclosed in the U.S. Pat. Nos. 4,737,794 and 5,307,072.

It will be recalled that the contributions of the various generators 3 are preferentially differentiated thanks to their different frequencies.

Six degrees of freedom are preferentially extracted for the location in position and in attitude of the object 1 from the nine coefficients of a matrix (called "signal matrix" in the aforementioned documents) derived from the demodulation of the signals received by the three coils of the sensor 2 with respect to the three coils of the generator 3.

As will be seen, the present multi-source system is going to "merge" the location results by each mono-source sub-system in an astute manner to obtain a "unified" position/orientation.

It should be noted that the method preferentially includes the prior harmonisation of the generators 3 in order to be able to represent the locations with respect to all the sources in the common reference frame. Indeed, the common reference frame is indispensable to verify the mutual compatibility of the mono-source results and to merge them in an intelligent manner.

The harmonisation is carried out in calibration. The positions and the attitudes of all the sources are determined with respect to an absolute point of reference, which may be chosen according to the application.

In the remainder of the description, mention will only be made of the position of the object 1, but it will be understood that the present method also advantageously takes into consideration the attitude, and those skilled in the art will consequently know how to transpose it.

Mono-Source Integrity

In a step (b), a parameter is estimated by the data processing means 21 for each generator 3 representative of an error on said determined position (and if needs be on said attitude) of the sensor 2 for the generator 3. In other words, an error parameter is associated with each of the n generators 3. Said parameter may be seen as an error level, and may be directly an estimation of the position error (expressed as a distance) and/or of the attitude error (expressed as an angle).

This parameter makes it possible to distinguish sources of which the integrity is compromised (abnormally high error, for example on account of the presence of a metal disturbance near to the generator 3), from those of which the integrity is confirmed (error within acceptable tolerance levels).

Indeed, the Applicant has noted the physical fact according to which, in a mono-source system, the error due to a local disturbance is asymmetric with respect to the centre of the disturbance: it is larger on the side further away from the source than on the side between the source and the disturbance. In other words, a local disturbance arranged between the source and the sensor is going to have a strong impact on the measurement, but a local disturbance arranged beyond the sensor is not going to have a substantial impact on the measurement associated with this source.

Thus, the present method proposes not seeking to correct the disturbances or even to detect them as was the case in the prior art, but simply to play on the redundancy of the generators 3 so as to base permanently the location uniquely on the basis of reliable measurements, i.e. to exclude "disturbed sources".

From the moment that there is an arrangement of the generators suited to typical locations of disturbances (for example by surrounding the zone in which the object 1 is intended to be displaced), such a solution is very robust (any type of disturbance, including potential deficiencies of a generator 3) and very easy to implement. In addition, and as will be seen later, it is modulable as a function of the desired precision levels (according to the desired application).

In experience, a reduction in the error by a factor between two and five is observed.

To do so, as described above, the mono-source calculation extracts the six degrees of freedom for the location in position and in attitude from the nine coefficients of a matrix derived from the demodulation of the signals received by the three coils of the sensor with respect to the three coils of the generator 3. Yet, among the redundant degrees of freedom (three), there are two mathematical invariants, that is to say quantities which have theoretically constant values. The estimation of these invariants with the measured data makes it possible to test the integrity of the measurement (by comparison with the theoretical values that they should have had in a perfect model) and thereby provide an estimation of the error.

$M_{ij}$ will designate the amplitude of the magnetic field derived from the coil j of a generator 3 and measured by the coil i of the sensor 2, with i,j=1,2,3 for the axes x, y, z of the two points of reference. It may be that there are n matrices $M_k$, each associated with one of the n generators 3.

If it is assumed that each generator 3 comprises three perfectly orthogonal coils which emit a perfectly dipolar magnetic field and that the triaxial sensor is also perfect, each matrix M has the form (see for example U.S. Pat. No. 4,737,794):

$$M = A^T \cdot \frac{k}{r^5} \begin{pmatrix} 3x^2 - r^2 & 3xy & 3xz \\ 3xy & 3y^2 - r^2 & 3yz \\ 3xz & 3yz & 3z^2 - r^2 \end{pmatrix}.$$

Here, A denotes the orthogonal matrix for the attitude of the sensor with respect to the point of reference of the source. The parameter k is the dipolar moment multiplied with $\mu/4\pi$ and $r=\sqrt{x^2+y^2+z^2}$ and the distance between the source and the sensor, the latter being found in (x, y, z) in the point of reference of the source.

A breakdown into singular values of the matrix M gives $$M = P \begin{pmatrix} s_1 & 0 & 0 \\ 0 & s_2 & 0 \\ 0 & 0 & s_3 \end{pmatrix} Q^T,$$

where P, Q are orthogonal matrices whereas the singular values are equal to $s_1=2k/r^3$ and $s_2=s_3=k/r^3$. The ratios $s_1/s_2=2$ and $s_1/s_3=2$ thus have predefined values and are said mathematical invariants inherent in the dipolar model for the magnetic field. It will be understood that those skilled in the art will be able to find other values of mathematical invariants, for example $s_2/s_1=0.5$ and $s_2/s_3=1$, $s_1-2s_2=0$ and $s_1-2s_3=0$, etc. Generally speaking, any mathematical invariant obtained from the singular values of the matrix of measured magnetic field data could be taken.

A deviation of the invariants with respect to their theoretical values indicates that the model is not valid, which may be due to a disturbance in the magnetic field (or any other problem linked to the generator 3).

To quantify the deviation, it is possible for example, if one notes $c_1^{est}$, $c_1^{est}$, $c_2^{est}$, $c_2^{th}$ the estimated and theoretical values of the first and second invariants, to introduce the function:

$$f(M) = (c_1^{th} - c_1^{est})^2 + (c_2^{th} - c_2^{est})^2 = \left(2 - \frac{s_1}{s_2}\right)^2 + \left(2 - \frac{s_1}{s_3}\right)^2$$

in our preferred example; or similar functions, which make it possible to estimate the deviations of the mathematical invariants $s_1/s_2$ and $s_1/s_3$. More specifically, any function could be chosen such that in the perfect case $$\left(\text{i.e. } \frac{s_1}{s_2} = \frac{s_1}{s_3} = 2\right) f(M) = 0,$$

and otherwise $f(M)>0$, with $f$ increasing when the deviation between the estimated values of the invariants (from the measured data) and their theoretical values (in this case 2) increase.

For example, the function $f(M)=|c_1^{th}-c_1^{est}|+|c_2^{th}-c_2^{est}|$ could alternatively be taken.

The function $f(M)$ or any similar function is a preferred example of parameter representative of a position/attitude error.

The function $f(M)$ even enables an estimation of the error $\Delta x$ in position and the error $\Delta\varphi$ in attitude:

$$\Delta x \approx C_1 r f(M);$$

$$\Delta\varphi \approx C_2 f(M).$$

The coefficients $C_1$ and $C_2$ may be determined by simulation or by experiment and adapted to the desired level of confidence.

Thus, step (b) advantageously includes the calculation of $\{f(M_k)\}_{k \in [[1;n]]}$, or even that of $\{\Delta x_k\}_{k \in [[1;n]]}$ and/or $\{\Delta\varphi_k\}_{k \in [[1;n]]}$.

In a realistic situation, magnetic fields do not correspond to perfect dipoles. Conversely, deviations in the dipolar field may be modelled and corrected in calibration and the integrity criterion will be calculated for a corrected matrix M. In this case, the function $f(M)$ also quantifies the deviation of the model and thus enables an estimation of the error.

It will be noted that for physical reasons, mono-source methods only enable a location with an ambiguity on the half-space, because the magnetic field does not make it possible to distinguish the positions (x, y, z) and (−x, −y, −z) (in the common point of reference), this constraint is physically inevitable for dipolar fields.

The present multi-source system does not suffer from this ambiguity, because the bad half-space for one or more generators 3 would lead to an incompatibility of the mono-source locations with deviations of the order of the metre whereas for the good half-spaces, the compatibility is typically verified to the sub-millimetric order or, in the case of (local) disturbances, to the at least centimetric order.

Multi-Source Selection and Merging

The mono-source estimation of error will be used to preselect the sources that will be taken into account in the multi-source calculation.

In a step (c) a sub-set of the set of generators 3 is selected as a function of said parameters estimated for each of the generators 3. The idea is to dismiss if needs be potential sources of which the integrity is compromised.

Once the results for the location of the sensor with respect to all the selected generators 3 are available in a common point of reference, they will be merged in a final result which can include an estimation of the error. Step (d) thereby includes the estimation of the position of the object 1 by merging the determined positions of the sensor 2 for each generator 3 selected in said sub-set. More precisely, a unified position of the sensor 2 is determined, and the position of the object 1 is deduced therefrom (by a simple offset). It is necessary to understand that merging is taken to mean the combination of several "complete" position measurements calculated with respect to the generators 3 in particular triaxes. This arrangement must not be confused with the combination of magnetic measurements with respect to several monoaxial magnetic generators to calculate a single position as is found in the prior art (this does not constitute a merger of several positions, but the simple reconstitution of a single position).

Said sub-set of the set of generators 3 selected at step (c) preferentially includes each generator 3 for which said estimated parameter is less than at least one reference threshold, designated "precision target", for example 1 mm in position and/or 1° in attitude.

II may be desirable that said sub-set contains at least one predetermined minimum number N of generators 3, for example N=2 (in particular if n=3) or N=3 (in particular if n>3).

Figure 2:
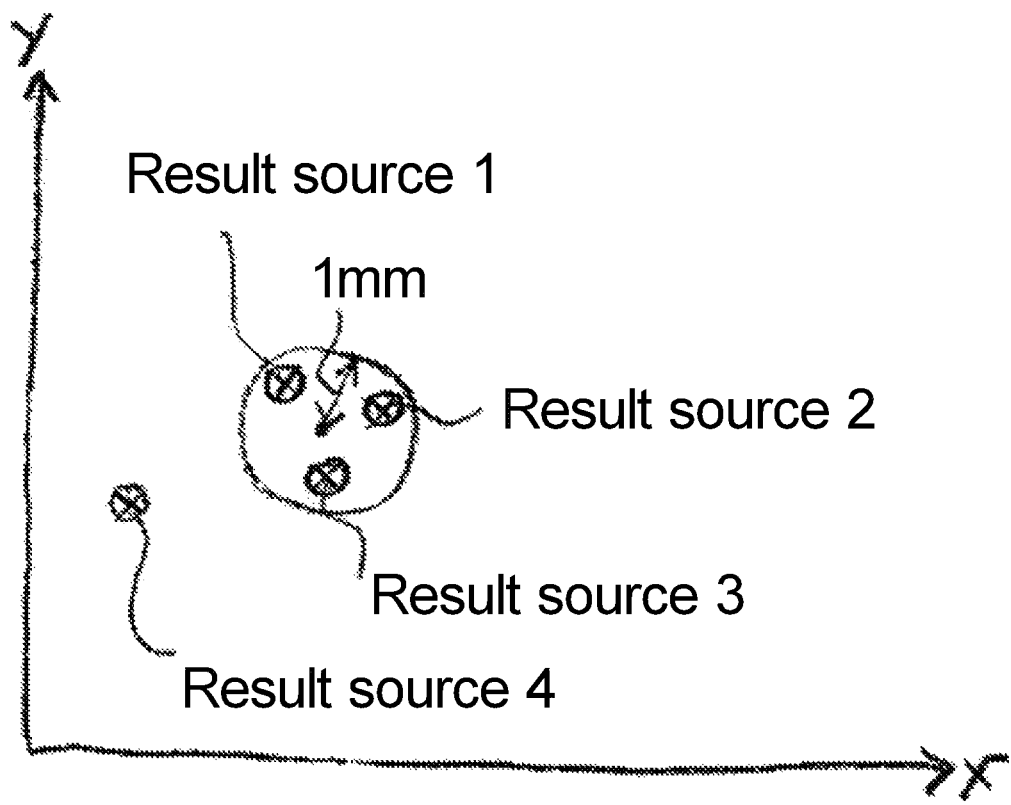
FIG. 2 illustrates in greater detail an exemplary embodiment of the method according to the invention.

If this is the case of said selected sub-set, then everything is well and one can move on to step (d). In the example of FIG. 2, the results for the position of the sources 1-3 are compatible with respect to a reference threshold of 1 mm. The source 4 is not compatible, possibly due to a disturbance of its field by a metal object between the sensor and this source. This disturbance, which would inflict an error of several millimetres on a location with only the source 4, has no impact on the multi-source measurement.

If this is not the case (said sub-set contains less than the predetermined minimum number N of generators 3), it is desirable to add more thereof even if other generators 3 are associated with a lower precision.

Thus, if said sub-set includes fewer than a predetermined minimum number of generators 3, said sub-set of the set of generators 3 selected at step (c) further includes at least one (or even each) generator 3 for which said estimated parameter is less than at least one degraded threshold greater than the reference threshold, designated "degraded target" for example 1.5 mm in position and/or 1.5° in attitude.

There may be several degraded thresholds, and these thresholds (from the lowest to the highest) may be considered successively until said predetermined minimum number N of generators is reached.

In other words, said sub-set of the set of generators 3 selected at step (c) includes each generator 3 for which said estimated parameter is less than the lowest threshold among a plurality of predetermined thresholds such that said sub-set includes at least one predetermined minimum number of generators 3.

It will be understood that other calculation modes could be taken into account by those skilled in the art, for example by sorting the generators 3 according to the value of the associated position error, taking for example the N with the lowest error.

As regards the merger of step (d), an easy way to proceed is to take the average position of the determined positions (and if needs be to take the average attitude of the determined attitudes) of the sensor 2 for each generator 3 selected in said sub-set.

This can only be valid if the sub-set only includes generators 3 for which the position error is below the reference threshold.

If on the other hand said sub-set of the set of generators 3 selected at step (c) includes at least one generator 3 for which said estimated parameter is greater than said reference threshold (i.e. less than a degraded threshold), it may be determined that the merged value will be the average of the largest compatible sub-set (i.e. or, in the case of equality between two or more sub-sets, the average of the sub-set with a minimum (co-)variance).

It will be understood that other calculation modes could be taken into account by those skilled in the art, for example by weighting the determined positions in the calculation of the unified position according to whether the associated generator 3 has a position error above or below the reference threshold. It is even possible for example to envisage weighting the determined positions with the inverse of the error.

In a particularly preferred manner, the algorithm thereby tracks the following points for each measurement sample:

1. Choice of a reference threshold, for example 1 mm/1°
2. Preselection of generators 3. Only these generators for which the estimation of the error is compatible with the reference threshold will be accepted for the remainder. If the number of preselected generators 3 is less than the predetermined minimum number (for example three), the algorithm returns to point 1 with a degraded threshold, for example 1.5 mm/1.5°.
3. Test if the results of the preselected generators 3 are compatible with respect to the predetermined threshold.
   a. If yes, the result will be the average of the positions associated with the preselected generators 3 with the estimation of the error given by the reference threshold.
   b. If not, test if a sub-set of preselected generators 3 of a number N' equal to or less than the predefined number N (for example N'=2) is compatible with respect to the reference threshold.
      i. If yes, the result will be the average of the positions associated with the generators 3 of the largest compatible sub-set or, in the event of equality between two or more sub-sets, the average of the positions associated with the generators 3 of the sub-set with a minimum (co-)variance. The estimated error will be the precision target.
      ii. If not, the algorithm will return to point 1 with a degraded threshold.

The algorithm is modifiable with respect to the level of confidence (which enters into the compatibility tests), the predetermined minimum number N and the thresholds.

If the algorithm does not find a location compatible with the worst of the thresholds (degraded), only a threshold less than the error could be supplied. By adapting the thresholds to the scale of the expected or tolerated errors, this case may be avoided or not present a defect. If, for example, a precision better than 1 mm is the only constraint for the operation of an application, it suffices to test the target from 1 mm and, if it cannot be reached due to a disturbance, to reject the measurement.

Equipment and System

According to a second aspect, the invention relates to in particular a system for the implementation of one or the other of the embodiments of the method.

As explained previously, the system includes a triaxial magnetic sensor 2 and a set of at least three triaxial magnetic generators 3 static in a common reference frame for the location of an object 1 integral with the sensor 2 and moving in the magnetic field generated by said generators 3.

The system includes, potentially in a remote manner, data processing means 21 configured for the implementation of the steps of the method, and if needs be data storage means 22 and/or communication means for the exportation of the results.

The data processing means 21 of the system are configured to implement:

A module for determining, for each generator 3, a position of said sensor 2 in said common reference frame as a function of magnetic field measurements acquired by the sensor 2 and associated with said generator 3;

A module for calculating, for each generator 3, a parameter representative of an error on said determined position of the sensor 2 for the generator 3;

A module for selecting a sub-set of the set of generators 3 as a function of said parameters estimated for each of the generators 3;

A module for estimating the position of the object 1 by merging the determined positions of the sensor 2 for each generator 3 selected in said sub-set.

Computer Programme Product

According to a third and a fourth aspect, the invention relates to a computer programme product including code instructions for the execution (on the processing means 21) of a method for locating an object 1 integral with a triaxial magnetic sensor 2 moving in a magnetic field generated by a set of at least three triaxial magnetic generators 3 static in a common reference frame according to the first aspect of the invention, as well as storage means readable by a computer equipment (for example data storage means 22) on which this computer programme product is found.

The invention claimed is:

1. A method for locating an object integral with a triaxial magnetic sensor moving in a magnetic field generated by a set of at least three triaxial magnetic generators static in a common reference frame, wherein the method includes the steps of:
   (a) for each triaxial magnetic generator of the set, determining as a function of magnetic field measurements acquired by the triaxial magnetic sensor and associated with said triaxial magnetic generator a position of said triaxial magnetic sensor in said common reference frame;
   (b) calculating for each triaxial magnetic generator of the set a parameter representative of an error on said determined position of the triaxial magnetic sensor for the triaxial magnetic generator;
   (c) selecting a sub-set of the set of triaxial magnetic generators as a function of said parameters estimated for each of the triaxial magnetic generators, said selected sub-set of the set of triaxial magnetic generators including each triaxial magnetic generator for which said estimated parameter is less than at least one reference threshold; and
   (d) estimating the position of the object by merging the determined positions of the triaxial magnetic sensor for each triaxial magnetic generator in said selected sub-set.

2. The method according to claim 1, in which the triaxial magnetic sensor and the triaxial magnetic generators are each constituted of three coils organised into triaxes.

3. The method according to claim 1, in which step (b) includes for each triaxial magnetic generator the estimation of the values of two mathematical invariants as a function of the magnetic field measurements acquired by the triaxial magnetic sensor and associated with said triaxial magnetic generator.

4. The method according to claim 3, in which said parameter representative of an error on said determined position of the triaxial magnetic sensor is calculated for each triaxial magnetic generator at step (b) as a function of the estimated values of said two mathematical invariants for said triaxial magnetic generator and theoretical values of said two mathematical invariants.

5. The method according to claim 1, in which said parameter representative of an error on said determined position of the triaxial magnetic sensor is an estimation of said error on said determined position of the triaxial magnetic sensor.

6. The method according to claim 1, in which, if said sub-set includes fewer than a predetermined minimum number of triaxial magnetic generators, said sub-set of the set of triaxial magnetic generators selected at step (c) further includes each triaxial magnetic generator for which said estimated parameter is less than at least one degraded threshold greater than the at least one reference threshold.

7. The method according to claim 1, in which the position obtained by merging is the average position of the determined positions of the triaxial magnetic sensor for each triaxial magnetic generator in said selected sub-set.

8. The method according to claim 6, in which, if said sub-set of the set of triaxial magnetic generators selected at step (c) includes at least one triaxial magnetic generator for which said estimated parameter is greater than said a least one reference threshold, the position obtained by merging is the average position of the determined positions of the triaxial magnetic sensor for each triaxial magnetic generator of the largest sub-set of said sub-set of triaxial magnetic generators for which said estimated parameter remains less than said reference at least one threshold.

9. The method according to claim 1, in which the attitude is taken into account in addition to the position in steps (a) to (d).

10. A non-transitory computer readable medium including code instructions for the execution of the method according to claim 1, when said non-transitory computer-readable medium is read by a computer.

11. A system including a triaxial magnetic sensor, a set of at least three triaxial magnetic generators static in a common reference frame, for the location of an object integral with the triaxial magnetic sensor and moving in the magnetic field generated by said triaxial magnetic generators, said system including data processing means configured to implement:
   a module for determining, for each triaxial magnetic generator, a position of said triaxial magnetic sensor in said common reference frame as a function of magnetic field measurements acquired by the triaxial magnetic sensor and associated with said triaxial magnetic generator;
   a module for calculating, for each triaxial magnetic generator, a parameter representative of an error on said determined position of the triaxial magnetic sensor for the triaxial magnetic generator;
   a module for selecting a sub-set of the set of triaxial magnetic generators as a function of said parameters estimated for each of the triaxial magnetic generators; and
   a module for estimating the position of the object by merging the determined positions of the triaxial magnetic sensor for each triaxial magnetic generator in said selected sub-set.

* * * * *